US006829376B2

(12) United States Patent
Bartell

(10) Patent No.: US 6,829,376 B2
(45) Date of Patent: Dec. 7, 2004

(54) COMPUTER SOFTWARE SYSTEM, METHOD, AND PRODUCT FOR SCANNED IMAGE ALIGNMENT

(75) Inventor: Daniel M. Bartell, San Carlos, CA (US)

(73) Assignee: Affymetrix, Inc., Santa Clara, CA (US)

( * ) Notice: Subject to any disclaimer, the term of this patent is extended or adjusted under 35 U.S.C. 154(b) by 733 days.

(21) Appl. No.: 09/681,819

(22) Filed: Jun. 11, 2001

(65) Prior Publication Data

US 2002/0047853 A1 Apr. 25, 2002

Related U.S. Application Data

(60) Provisional application No. 60/242,973, filed on Oct. 24, 2000.

(51) Int. Cl.[7] ................................................. G06K 9/00
(52) U.S. Cl. ........................................ 382/128; 702/19
(58) Field of Search ................................ 382/128, 129, 382/133, 134, 181, 190, 195, 205, 209; 702/1, 19–28

(56) References Cited

U.S. PATENT DOCUMENTS 5,706,364 A * 1/1998 Kopec et al. ............... 382/159
6,090,555 A    7/2000 Fiekowsky et al.
6,349,144 B1   2/2002 Shams
6,591,196 B1 * 7/2003 Yakhini et al. ............... 702/28
2003/0059094 A1 * 3/2003 Cattell et al. ............... 382/128

* cited by examiner

Primary Examiner—Leo Boudreau
Assistant Examiner—Tom Y. Lu
(74) Attorney, Agent, or Firm—William R. McCarthy, III; Philip L. McGarrigle; Alan B. Sherr

(57) ABSTRACT

An image alignment tool is described for adjusting the alignment of a grid with an image. An initial grid aligner determines an initial, approximately aligned, position of the grid. An intensity scorer determines, for each of a plurality of test grid elements of the plurality of grid elements, a set of intensity scores. Each member of the set is based, at least in part, on intensities of pixels of one or more image features within the test grid element in one of the initial or additional positions. A combined-rank-score generator combines, for each of the initial and additional grid positions, members of sets of rank scores corresponding to the grid position in order to generate a combined rank score for the grid position. A grid alignment adjuster adjusts the alignment of the grid based on a comparison among the combined rank scores.

36 Claims, 7 Drawing Sheets

FIGURE 4A

| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
|---|---|---|---|---|---|---|---|---|---|---|---|---|---|---|---|---|---|---|---|---|---|---|---|---|---|
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |
| 0 | 4 | 4 | 4 | 4 | 4 | 4 | 4 | 4 | 0 | 0 | 0 | 0 | 0 | 0 | 0 | 0 | 4 | 4 | 4 | 4 | 4 | 4 | 4 | 4 | 0 |

FIGURE 4B

| 2 | 3 | 4 | 4 | 4 | 4 | 4 | 4 | 3 | 2 | 2 | 2 | 2 | 2 | 2 | 3 | 4 | 4 | 4 | 4 | 4 | 4 | 4 | 4 | 3 |
|---|---|---|---|---|---|---|---|---|---|---|---|---|---|---|---|---|---|---|---|---|---|---|---|---|
| 2 | 3 | 4 | 4 | 4 | 4 | 4 | 4 | 3 | 2 | 1 | 1 | 1 | 1 | 1 | 2 | 4 | 4 | 4 | 4 | 4 | 4 | 4 | 3 | 2 |
| 2 | 3 | 4 | 4 | 4 | 4 | 4 | 4 | 3 | 2 | 1 | 0 | 0 | 1 | 1 | 1 | 3 | 4 | 4 | 4 | 4 | 4 | 4 | 2 | 3 |
| 1 | 3 | 4 | 4 | 4 | 4 | 4 | 4 | 3 | 2 | 1 | 0 | 0 | 1 | 1 | 1 | 2 | 4 | 4 | 4 | 4 | 4 | 4 | 3 | 3 |
| 2 | 3 | 4 | 4 | 4 | 4 | 4 | 4 | 3 | 2 | 1 | 0 | 0 | 0 | 1 | 1 | 3 | 3 | 4 | 4 | 4 | 4 | 4 | 2 | 2 |
| 2 | 3 | 4 | 4 | 4 | 4 | 4 | 4 | 3 | 2 | 1 | 1 | 0 | 1 | 1 | 1 | 2 | 4 | 4 | 4 | 4 | 4 | 4 | 3 | 3 |
| 2 | 3 | 4 | 4 | 4 | 4 | 4 | 4 | 3 | 2 | 2 | 2 | 2 | 2 | 2 | 2 | 4 | 4 | 4 | 4 | 4 | 4 | 4 | 3 | 2 |
| 1 | 2 | 3 | 4 | 4 | 4 | 4 | 4 | 3 | 2 | 3 | 3 | 3 | 3 | 3 | 3 | 3 | 3 | 4 | 4 | 4 | 4 | 4 | 3 | 2 | 3 |

FIGURE 4C

| 2 | 3 | 4 | 4 | 4 | 4 | 4 | 4 | 3 | 2 | 2 | 2 | 2 | 2 | 2 | 3 | 4 | 4 | 4 | 4 | 4 | 4 | 4 | 4 | 3 |
|---|---|---|---|---|---|---|---|---|---|---|---|---|---|---|---|---|---|---|---|---|---|---|---|---|
| 2 | 3 | 4 | 4 | 4 | 4 | 4 | 4 | 3 | 2 | 1 | 1 | 1 | 1 | 1 | 2 | 4 | 4 | 4 | 4 | 4 | 4 | 4 | 3 | 2 |
| 2 | 3 | 4 | 4 | 4 | 4 | 4 | 4 | 3 | 2 | 1 | 0 | 0 | 1 | 1 | 1 | 3 | 3 | 4 | 4 | 4 | 4 | 4 | 2 | 3 |
| 1 | 3 | 4 | 4 | 4 | 4 | 4 | 4 | 3 | 2 | 1 | 0 | 0 | 1 | 1 | 1 | 2 | 4 | 4 | 4 | 4 | 4 | 4 | 3 | 3 |
| 2 | 3 | 4 | 4 | 4 | 4 | 4 | 4 | 3 | 2 | 1 | 0 | 0 | 0 | 1 | 1 | 3 | 3 | 4 | 4 | 4 | 4 | 4 | 2 | 2 |
| 2 | 3 | 4 | 4 | 4 | 4 | 4 | 4 | 3 | 2 | 1 | 1 | 0 | 1 | 1 | 1 | 2 | 4 | 4 | 4 | 4 | 4 | 4 | 3 | 3 |
| 2 | 3 | 4 | 4 | 4 | 4 | 4 | 4 | 3 | 2 | 2 | 2 | 2 | 2 | 2 | 2 | 4 | 4 | 4 | 4 | 4 | 4 | 4 | 3 | 2 |
| 1 | 2 | 3 | 4 | 4 | 4 | 4 | 4 | 3 | 2 | 3 | 3 | 3 | 3 | 3 | 3 | 3 | 3 | 4 | 4 | 4 | 4 | 4 | 3 | 2 | 3 |

FIGURE 5

TABLE 5A - GRID POSITION OF FIGURE 4B

| Test Grid Element | Pixel Intensities | Sum | Intensity Score (Mean) | Rank Score* |
|---|---|---|---|---|
| 310C (Bright) | 3 4 4 4 4 4 4 3 | 30 | 3.6875 | 1 |
|  | 3 4 4 4 4 4 4 3 | 30 |  |  |
|  | 3 4 4 4 4 4 4 3 | 30 |  |  |
|  | 3 4 4 4 4 4 4 3 | 30 |  |  |
|  | 3 4 4 4 4 4 4 3 | 30 |  |  |
|  | 3 4 4 4 4 4 4 3 | 30 |  |  |
|  | 3 4 4 4 4 4 4 3 | 30 |  |  |
|  | 3 4 4 4 4 4 4 3 | 30 |  |  |
|  | 2 3 4 4 4 4 3 2 | 26 |  |  |
| 312C (Dim) | 2 2 2 2 2 2 2 3 | 17 | 1.5781 | 1 |
|  | 2 1 1 1 1 1 1 2 | 10 |  |  |
|  | 2 1 0 0 1 1 1 3 | 9 |  |  |
|  | 2 1 0 0 1 1 1 2 | 8 |  |  |
|  | 2 1 0 0 1 1 1 2 | 8 |  |  |
|  | 2 1 0 1 1 1 1 2 | 9 |  |  |
|  | 2 1 1 2 2 2 2 2 | 14 |  |  |
|  | 2 2 2 2 2 2 2 2 | 16 |  |  |
|  | 3 3 3 3 3 3 3 3 | 24 |  |  |
| 310D (Bright) | 4 4 4 4 4 4 4 4 | 32 | 3.7813 | 1 |
|  | 4 4 3 4 4 4 4 4 | 31 |  |  |
|  | 3 4 2 4 4 4 4 4 | 29 |  |  |
|  | 4 4 3 4 4 4 4 4 | 31 |  |  |
|  | 3 4 2 4 4 4 4 4 | 29 |  |  |
|  | 4 4 3 4 4 4 4 4 | 31 |  |  |
|  | 4 4 2 4 4 4 4 4 | 31 |  |  |
|  | 3 4 3 4 4 4 4 3 | 28 |  |  |

COMBINED RANK SCORE FOR GRID POSITION OF FIGURE 4B[++] ——————————> 3

TABLE 5B - GRID POSITION OF FIGURE 4C

| Test Grid Element | Pixel Intensities | Sum | Intensity Score (Mean) | Rank Score* |
|---|---|---|---|---|
| 310C (Bright) | 4 4 4 4 4 4 3 2 | 29 | 3.5938 | 2 |
|  | 4 4 4 4 4 4 3 2 | 29 |  |  |
|  | 4 4 4 4 4 4 3 2 | 29 |  |  |
|  | 4 4 4 4 4 4 3 2 | 29 |  |  |
|  | 4 4 4 4 4 4 3 2 | 29 |  |  |
|  | 4 4 4 4 4 4 3 2 | 29 |  |  |
|  | 4 4 4 4 4 4 3 2 | 29 |  |  |
|  | 3 4 4 4 4 3 2 3 | 27 |  |  |
| 312C (Dim) | 2 2 2 2 2 3 4 | 19 | 1.7656 | 2 |
|  | 1 1 1 1 1 2 4 | 12 |  |  |
|  | 1 0 0 1 1 2 4 | 10 |  |  |
|  | 1 0 0 1 1 2 4 | 10 |  |  |
|  | 1 0 0 1 1 3 3 | 9 |  |  |
|  | 1 1 0 1 1 3 4 | 11 |  |  |
|  | 2 2 2 2 2 4 4 | 18 |  |  |
|  | 3 3 3 3 3 3 3 | 24 |  |  |
| 310D (Bright) | 4 4 4 4 4 4 3 | 31 | 3.6563 | 2 |
|  | 4 4 4 4 4 3 2 | 29 |  |  |
|  | 4 4 4 4 4 2 3 | 29 |  |  |
|  | 4 4 4 4 4 3 3 | 30 |  |  |
|  | 4 4 4 4 4 2 2 | 28 |  |  |
|  | 4 4 4 4 4 3 3 | 30 |  |  |
|  | 4 4 4 4 4 3 2 | 29 |  |  |
|  | 4 4 4 4 3 2 3 | 28 |  |  |

COMBINED RANK SCORE FOR GRID POSITION OF FIGURE 4C[**] ——————————> 6

*Ranking: For bright cells, brightest test grid position is ranked "1"; for dim cells, dimmest test grid position is ranked "1".
**Lowest combined rank score determines adjusted grid position.

US 6,829,376 B2

COMPUTER SOFTWARE SYSTEM, METHOD, AND PRODUCT FOR SCANNED IMAGE ALIGNMENT

CROSS REFERENCE TO RELATED APPLICATIONS

The present application relates to and claims priority from provisional U.S. patent application Serial No. 60/242,973, filed Oct. 24, 2000, the complete disclosure of which is hereby incorporated herein by reference for all purposes.

BACKGROUND OF INVENTION

1. Field of the Invention

The present invention relates to the field of computerized image alignment. In particular, the present invention relates to computer systems, methods, and products for aligning grids on scanned images of high-density arrays of biological materials.

2. Related Art

A variety of systems are known for synthesizing or depositing dense arrays of biological materials, sometimes referred to as probes, on a substrate or support. Labeled targets in hybridized probe-target pairs may be detected using various commercial devices, referred to for convenience hereafter as scanners. Scanners image the targets by detecting fluorescent or other emissions from the labels. Data representing the detected emissions are stored in a memory device for processing. The processed images may be presented to a user on a video monitor or other device, and/or operated upon by various data processing products or systems. Some techniques are known for identifying the data representing detected emissions and separating them from background information. For example, U.S. Pat. No. 6,090,555 to Fiekowsky, et al. describes various of these techniques.

SUMMARY OF INVENTION

The present invention is directed in one embodiment to a method for adjusting the alignment of a grid with an image. Generally speaking, this method seeks an alignment that provides maximum contrast between bright and dim features rather than seeking to identify boundaries, per se, between bright and dim features. The grid in accordance with this method includes grid elements, such as grid squares in an example illustrated below. The image includes image features made up of pixels. For example, the image may include a checkerboard pattern in which the image features are alternating bright and dim squares. Each of the squares is made up of a number of pixels. It will be understood, however, that the pattern is not limited to a checkerboard, and that the image features may be any shape or combination of shapes.

The method includes the step of (1) determining an initial position of the grid. This determination may be made in some implementations such that the grid elements are at least approximately aligned with the plurality of image features. The term approximately is used broadly in this context to mean that, in a typical application, a significant portion of the grid elements are not out of alignment in a particular dimension with respect to image features by more than half the length of the features in that direction. Thus, the grid elements may be significantly out of alignment in one or both dimensions of, for example, a planar grid, but yet be approximately aligned as the term is used herein. It will be understood that although the examples described herein are drawn for convenience to two-dimensional images, the invention is not so limited. Rather, the images and alignment grids may be employed in three or more dimensions.

Additional steps in the method include the following. (2) One or more additional positions of the grid are determined so that each additional position is offset from the initial position and from other additional positions. (3) For each of two or more test grid elements of the two or more grid elements, a set of intensity scores is determined. Each member of this set is based, at least in part, on intensities of pixels of one or more image features within the test grid element in one of the initial or additional positions. (4) For each of the test grid elements, the set of intensity scores is ranked with respect to each other to generate a set of rank scores for the test grid element. (5) For each of the initial and additional grid positions, the members of the sets of rank scores corresponding to the grid position are combined to generate a combined rank score for the grid position. (6) The alignment of the grid is adjusted based, at least in part, on a comparison among the combined rank scores of the initial and additional grid positions.

The first step in this method may be accomplished in accordance with any of variety of known, or yet to be developed, techniques for aligning grids with images. For example, a technique described in U.S. Pat. No. 6,090,555, may be used. The '555 patent is hereby incorporated by reference herein in its entirety for all purposes. In accordance with one method of the '555 patent, the image includes a first pattern. Steps in that method include (a) convolving the image with a filter to generate a second image having a second pattern, (b) identifying the second pattern, (c) aligning the grid over the image according to a position of the second pattern, and (d) adjusting the position of the grid to minimize a sum of the intensities of pixels along a direction in the grid. Thus, in this example, steps (a) through (c) implement step (1) of the method described with respect to the present invention.

In some implementations of the method of the present invention, step (2) includes moving the grid from the first grid position in a positive or negative X direction by a value substantially equal to a span of one or more pixels, moving the grid from the first grid position in a positive or negative Y direction by a value substantially equal to a span of one or more pixels, or both. In aspects of these implementations, the test grid elements each have a first length in the X direction and a second length in the Y direction. Step (2) in these aspects further includes moving the grid from the first grid position in the positive or negative X direction by a value no greater than approximately half the first length, moving the grid from the first grid position in the positive or negative Y direction by a value no greater than approximately half the second length, or both.

Step (3) may include determining, for at least one member of the set of intensity scores, a mean of intensity values of pixels within the test grid element. Also, step (3) may include the following two steps: (a) based on the initial grid position, identifying each of the plurality of grid elements as either a dim grid element or, in the alternative, a bright grid element; and (b) selecting the test grid elements based, at least in part, on including dim grid elements when they are bordered on all sides by a bright grid element. In other implementations, the dim grid elements may be including among the test grid elements if they are bordered on fewer than all sides, or on no side, by a bright grid element. Some bright grid elements may also not be included among the test grid elements in some implementations.

In some aspects of the preceding method, step (3)(a) may include the further steps of (i) based on a determined pattern (such as, for example, a checkerboard), associating each of the plurality of grid elements with one of either a first element group or a second element group; (ii) determining a first intensity of one or more of the grid elements in the first element group and a second intensity of one or more of the grid elements in the second element group; (iii) comparing the first and second intensities; (iv) designating the grid elements in the first element group as dim grid elements when the first intensity is less than the second intensity and as bright grid elements when the first intensity is greater than the second intensity; and (v) designating the grid elements in the second element group as dim grid elements when the second intensity is less than the first intensity and as bright grid elements when the second intensity is greater than the first intensity. Step (3) (a)(ii) may include determining a median of intensities of three or more pixels, or every pixel, within each of the one or more grid elements in the first and second element groups. Similarly, in other aspects, step (3)(a)(ii) may include determining a median of intensities of three or more pixels, or every pixel, within each grid element in the first and second element groups. The first intensity may include a first overall median of the medians of intensities of pixels within each grid element in the first element group. The second intensity may include a second overall median of the medians of intensities of pixels within each grid element in the second element group.

In some implementations, step (4) of the method of the present invention may further include the step of ranking the sets of intensity scores of test grid elements identified as dim grid elements in an opposite sense to the ranking of sets of intensity scores of test grid elements identified as bright grid elements. For example, grid elements determined to be bright elements may be ranked by sorting their intensities in order of decreasing intensity with the element having the brightest intensity score ranked lowest (e.g., 1). Grid elements determined to be dim elements may be ranked by sorting their intensities in order of increasing intensity with the element having the dimmest intensity score ranked lowest (e.g., Another embodiment of the present invention is directed to an image alignment tool for adjusting the alignment of a grid with an image. The grid includes a plurality of grid elements and the image includes a plurality of image features comprised of pixels. The image alignment tool includes an initial grid aligner that determines an initial position of the grid. Also included is a grid offsetter that determines one or more additional positions of the grid that each are offset from the initial position and from each other. An intensity scorer also is included that, for each of a plurality of test grid elements of the plurality of grid elements, determines a set of intensity scores. Each member of the set is based, at least in part, on intensities of pixels of one or more image features within the test grid element in one of the initial or additional positions. Another element of the tool is an intensity-score ranker that, for each of the test grid elements, ranks the set of intensity scores with respect to each other to generate a set of rank scores for the test grid element. Yet another element is a combined-rank-score generator that, for each of the initial and additional grid positions, combines the members of the sets of rank scores corresponding to the grid position to generate a combined rank score for the grid position. The image alignment tool of this embodiment also includes a grid alignment adjuster that adjusts the alignment of the grid based, at least in part, on a comparison among the combined rank scores of the initial and additional grid positions.

The invention is directed in yet further embodiments to a computer program product for adjusting the alignment of a grid with an image. The computer program product typically is embodied in a computer-readable medium, such as a CD-ROM, a disk, or in internal RAM or other memory. Moreover, the product may be implemented in other forms, such as firmware or a combination of firmware and software. The grid includes grid elements, and the image includes image features made up of pixels. The method includes the following steps. (1) An initial position of the grid is determined such that the grid elements are at least approximately aligned with the plurality of image features. (2) One or more additional positions of the grid are determined so that each additional position is offset from the initial position and from other additional positions. (3) For each of two or more test grid elements of the two or more grid elements, a set of intensity scores is determined. Each member of this set is based, at least in part, on intensities of pixels of one or more image features within the test grid element in one of the initial or additional positions. (4) For each of the test grid elements, the set of intensity scores is ranked with respect to each other to generate a set of rank scores for the test grid element. (5) For each of the initial and additional grid positions, the members of the sets of rank scores corresponding to the grid position are combined to generate a combined rank score for the grid position. (6) The alignment of the grid is adjusted based, at least in part, on a comparison among the combined rank scores of the initial and additional grid positions.

In another embodiment, the invention is directed to a computer system for processing images. The computer system includes a data storage device that stores data representing an image that has image features comprised of pixels. The computer system also has an image alignment tool, in accordance with the present invention, for adjusting the alignment of a grid with the image. In a yet further embodiment, the invention is directed to a scanning system that includes an excitation source that produces emissions from labeled targets hybridized to probe features, and a detector that detects the emissions and generates data representing one or more characteristics of the emissions. The scanning system also includes a data storage device that stores an image having image features comprised of pixels based on data generated by the detector. Also included in the scanning system is an image alignment tool, in accordance with the present invention, for adjusting the alignment of a grid with the image.

A method is also described for analyzing an array of probes including biological polymers. The method includes: (a) contacting the array with targets including biological polymers under conditions effective for binding between the targets and the probes; (b) detecting an association between the targets and probes using an imaging system to produce data that represents the association, the data being capable of forming an image; (c) associating the data with a first set of locations on the array; (d) analyzing the data to determine a measure of contrast; and (e) re-associating the data with a second set of locations based, at least in part, on the measure of contrast. The above embodiments are not necessarily inclusive or exclusive of each other and may be combined in any manner that is non-conflicting and otherwise possible, whether they be presented in association with a same, or a different, aspect of the invention. The description of one embodiment is not intended to be limiting with respect to other embodiments. Also, any one or more function, step, operation, or technique described elsewhere in this specification may, in alternative embodiments, be combined with any one or more function, step, operation, or technique described in the summary. Thus, the above embodiments are illustrative rather than limiting.

BRIEF DESCRIPTION OF DRAWINGS

The above and further advantages of the invention will be more clearly appreciated from the following detailed description when taken in conjunction with the accompanying drawings. In the drawings, like reference numerals indicate like structures or method steps and the leftmost digit of a reference numeral indicate the number of the figure in which the referenced element first appears (for example, the element 180 appears first in FIG. 1).

FIG. 4A is a simplified graphical representation of one embodiment of an idealized version of the image of FIG. 3A showing illustrative intensity values of pixels in the file;

FIG. 4B is a simplified graphical representation of one embodiment of the image of FIG. 3A showing illustrative intensity values of pixels in the image;

FIG. 4C is a simplified graphical representation of one embodiment of the image of FIG. 3B showing illustrative intensity values of pixels in the image;

FIG. 5A is a table showing the numerical representations of illustrative intensity values of pixels as shown in FIG. 4B, and showing intensity scores and rank scores determined for grid elements of FIG. 4B by the image alignment tool of FIG. 2;

FIG. 5B is a table showing the numerical representations of illustrative intensity values of pixels as shown in FIG. 4C, and showing intensity scores and rank scores determined for grid elements of FIG. 4C by the image alignment tool of FIG. 2;

DETAILED DESCRIPTION

Figure 1:
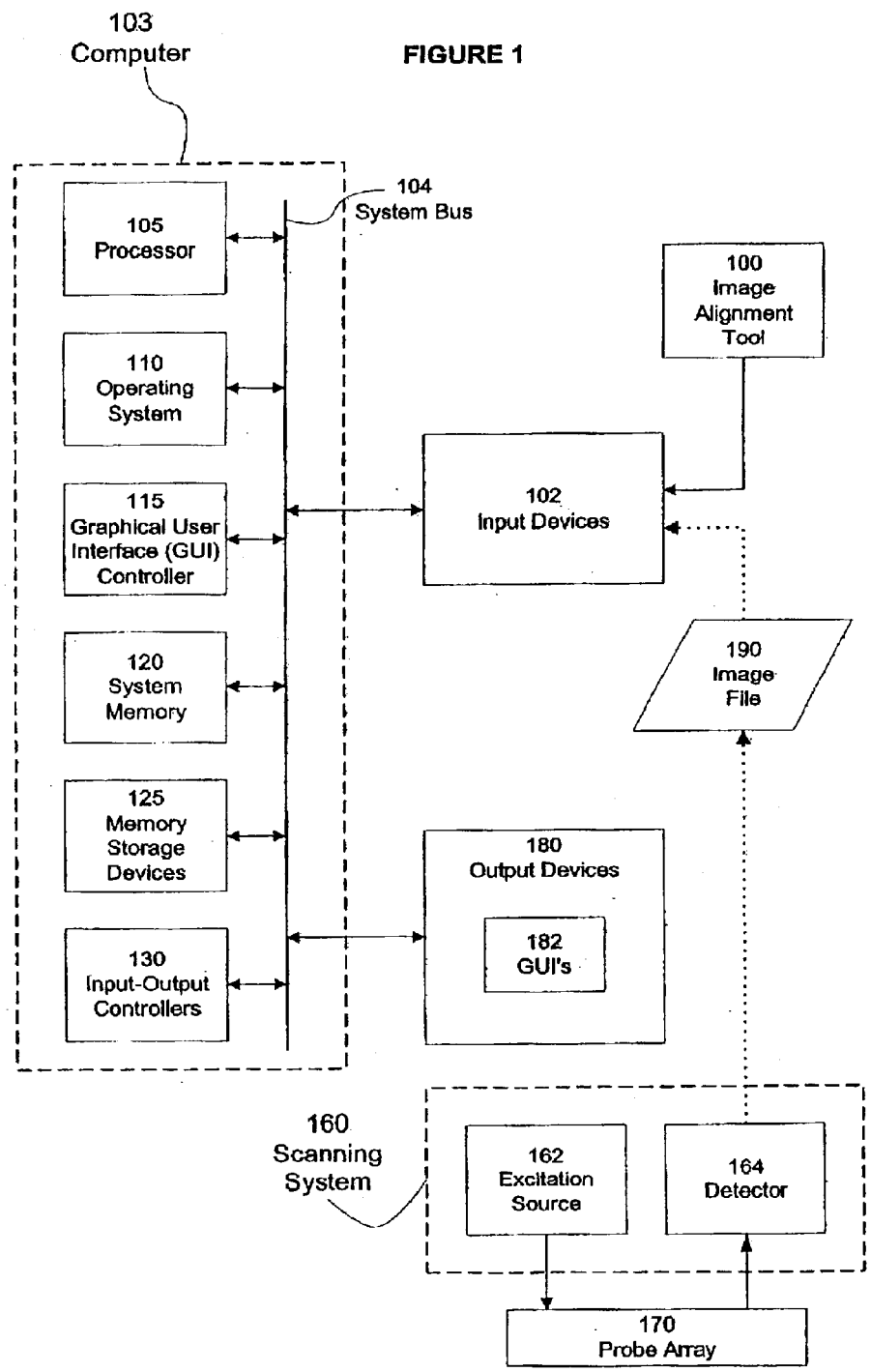
FIG. 1 is a functional block diagram of one embodiment of a computer system for implementing an illustrated embodiment of an image alignment tool in accordance with the present invention.

As noted, commercial systems are available for synthesizing or depositing dense arrays of biological materials on a substrate or support. For example, Affymetrix® GeneChip® arrays, manufactured by Affymetrix, Inc. of Santa Clara, Calif., are synthesized in accordance with various techniques sometimes referred to as VLSIPS™ (Very Large Scale Immobilized Polymer Synthesis) technologies. Some aspects of VLSIPS™ technologies are described in U.S. Pat. No. 5,143,854 to Pirrung, et al.; U.S. Pat. No. 5,445,934 to Fodor, et al.; U.S. Pat. No. 5,744,305 to Fodor, et al.; U.S. Pat. No. 5,831,070 to Pease, et al.; U.S. Pat. No. 5,837,832 to Chee, et al.; U.S. Pat. No. 6,022,963 to McGall, et al.; U.S. Pat. No. 6,083,697 to Beecher, et al. Each of these patents is hereby incorporated by reference in its entirety. Generally, the probes of these arrays consist of oligonucleotides synthesized by methods that include the steps of activating regions of a substrate and then contacting the substrate with a selected monomer solution. The regions are activated with a light source shown through a mask in a manner similar to photolithography techniques used in the fabrication of integrated circuits. Other regions of the substrate remain inactive because the mask blocks them from illumination. By repeatedly activating different sets of regions and contacting different monomer solutions with the substrate, a diverse array of polymers is produced on the substrate. Various other steps, such as washing unreacted monomer solution from the substrate, are employed in various implementations of these methods. For convenience, arrays synthesized according to these techniques, or ones now existing or that may be developed in the future based on a synthesis process, are referred to hereafter as synthesized arrays.

Other techniques exist for depositing probes on a substrate or support. For example, spotted arrays are commercially fabricated on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. The Affymetrix® 417™, 427™, and 437™ Arrayers from Affymetrix, Inc. are devices that deposit densely packed spotted arrays of biological material on a microscope slide in accordance with these techniques, aspects of which are described in PCT Application No. PCT/US99/00730 (published on Jul. 22, 1999 as International Publication Number WO 99/36760), hereby incorporated by reference in its entirety. Other techniques for generating spotted arrays also exist. For example, U.S. Pat. No. 6,040,193 to Winkler, et al. is directed to processes for dispensing drops to generate spotted arrays. The '193 patent, and U.S. Pat. No. 5,885,837 to Winkler, also describe the use of microchannels or micro-grooves on a substrate, or on a block placed on a substrate, to synthesize arrays of biological materials. These patents further describe separating reactive regions of a substrate from each other by inert regions and spotting on the reactive regions. The '193 and '837 patents are hereby incorporated by reference in their entireties. Another technique is based on ejecting jets of biological material to form a spotted array. Various implementations of the jetting technique may use devices such as syringes or piezo electric pumps to propel the biological material.

Spotted arrays or synthesized arrays typically are used in conjunction with tagged biological samples such as cells, proteins, genes, DNA sequences, or other biological elements. These samples, referred to herein as targets, are processed so that they are spatially associated with certain probes in the probe array. For example, one or more chemically tagged biological samples, i.e., the targets, are distributed over the probe array. Some targets hybridize with at least partially complementary probes and remain at the probe locations, while non-hybridized targets are washed away. These hybridized targets, with their tags or labels, are thus spatially associated with the targets" complementary probes. The hybridized probe and target may sometimes be referred to as a probe-target pair. Detection of these pairs can serve a variety of purposes. For example, detection of these pairs on appropriately synthesized arrays can be used to determine whether a target nucleic acid has a nucleotide sequence identical to or different from a specific reference sequence. See, for example, U.S. Pat. No. 5,837,832 to Chee, et al., incorporated by reference herein in its entirety for all purposes. Other uses include gene expression monitoring (see U.S. Pat. Nos. 5,800,992 and 6,040,138, hereby incorporated by reference herein in their entireties), genotyping (see U.S. Pat. No. 5,856,092, hereby incorporated by reference herein in its entirety), or other detection of nucleic acids.

To ensure proper interpretation of the term probe as used herein, it is noted that contradictory conventions exist in the relevant literature. The word probe is used in some contexts to refer not to the biological material that is synthesized on a substrate or deposited on a slide, as described above, but to what has been referred to herein as the target. To avoid confusion, the term probe is used consistently herein to refer to the oligonucleotides synthesized according to the VLSIPS™ technology, the biological materials deposited so as to create spotted arrays, and materials synthesized or deposited to form arrays according to similar technologies that now exist or may be developed in the future. Thus, arrays formed in accordance with any of these technologies may be referred to generally and collectively hereafter for convenience as probe arrays.

Labeled targets in hybridized probe-target pairs may be detected using any of a variety of commercial scanners. Scanners image the targets by detecting fluorescent or other emissions from the labels, or by detecting transmitted, reflected, or scattered radiation. These processes are generally and collectively referred to hereafter for convenience simply as involving the detection of emissions. Various detection schemes are employed depending on the type of emissions and other factors. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Other scanners or scanning systems are described in U.S. Pat. Nos. 5,578,832; 5,631,734; 5,834,758; 5,981,956 and 6,025,601, and in PCT Application PCT/US99/06097 (published as WO99/47964), each of which is hereby incorporated herein by reference in its entirety for all purposes.

The scanning system provides data representing the intensities (and possibly other characteristics, such as color) of the detected emissions, as well as the locations on the substrate where the emissions were detected. The data typically are stored in a memory device in the form of a data file. One type of data file, sometimes referred to as an image file, typically includes intensity and location information corresponding to elemental sub-areas of the scanned substrate. The term elemental in this context means that the intensities, and/or other characteristics, of the emissions from this area each are represented by a single value. When displayed as an image for viewing or processing, elemental picture elements, or pixels, often represent this information. Thus, for example, a pixel may have a single value representing the intensity of the elemental sub-area of the substrate from which the emissions were scanned. The pixel may also have another value representing another characteristic, such as color. For instance, a scanned elemental sub-area in which high-intensity emissions were detected may be represented by a pixel having high luminance (hereafter, a bright pixel), and low-intensity emissions may be represented by a pixel of low luminance (a dim pixel).

Alternatively, the chromatic value of a pixel may be made to represent the intensity, color, or other characteristic of the detected emissions. Thus, an area of high-intensity emission may be displayed as a red pixel and an area of low-intensity emission as a blue pixel. As another example, detected emissions of one wavelength at a particular sub-area of the substrate may be represented as a red pixel, and emissions of a second wavelength detected at another sub-area may be represented by an adjacent blue pixel. Many other display schemes are known.

Probes need not have been synthesized or deposited on all areas of the substrate. On an Affymetrix® GeneChip® array, for example, the synthesized region of the entire nucleic acid array typically is bordered by a non-synthesized area. Because the non-synthesized area does not contain probes, labeled targets do not hybridize there and the scanning-system ideally should not detect emissions. However, various imperfections may give rise to the detection of background emissions from non-synthesized areas, or from synthesized areas in which hybridization has not occurred. The term background noise may be used hereafter to refer to these detected background emissions and noise from other sources.

Generally, a human being may inspect a printed or displayed image constructed from the data in an image file and may identify those cells that are bright or dim, or are otherwise identified by a pixel characteristic (such as color). However, it frequently is desirable to provide this information in an automated, quantifiable, and repeatable way that is compatible with various image processing and/or analysis techniques. For example, the information may be provided to a computer that associates the locations where hybridized targets were detected with known locations where probes of known identities were synthesized or deposited. Information such as the nucleotide or monomer sequence of target DNA or RNA may then be deduced. Techniques for making these deductions are described, for example, in U.S. Pat. No. 5,733,729 to Lipshutz, which hereby is incorporated by reference in its entirety for all purposes, and in U.S. Pat. No. 5,837,832, noted and incorporated above. Among other purposes, the data may be used to study genetic characteristics and to detect mutations relevant to genetic and other diseases or conditions.

In order to facilitate computer processing of the pixel information, it therefore typically is desirable to automate the identification of pixels having particular characteristics and relate them to the known locations of probes. To this end, computer-implemented image processing techniques have been developed to align the scanned image file. That is, the techniques attempt to identify which pixels represent emissions from which probes, and to distinguish this information from background noise. Some of these techniques are described in U.S. Pat. No. 6,090,555 to Fiekowsky, et al., incorporated by reference above. Generally speaking, one aspect of the technique described in the '555 patent operates on a pattern, such as a checkerboard pattern, that is known to be included in the scanned image. When the image is convolved with a filter, a recognizable pattern, such as a grid pattern, is generated in the convolved image. The scanned image may then be aligned according to the position of the recognizable pattern in the convolved image. In some implementations of these techniques, a grid is aligned over the scanned image and the position of the grid is adjusted to minimize a sum of the intensities of pixels along a grid direction.

Applications of this and other techniques may be complicated, however, when extreme, aberrant, or unexpected conditions are encountered during the scanning process, or when features of alignment patterns have indistinct edges for any of a variety of reasons. One cause of these complications is that the scanner may read alignment patterns, such as a checkerboard pattern, such that features of the pattern overlap. For example, if there is mechanical jitter in the scanner, the bright elements of the checkerboard pattern may be read as overlapping into adjoining dim elements even though the pattern of bright and dim emissions has no overlap.

As another example, difficulties may be encountered due to difficulties in establishing the boundaries between features when they are synthesized or deposited. For instance, it may be intended that a first feature be synthesized to consist of probes having a first sequence of bases, and an adjoining second feature be synthesized to consist of probes having a second sequence of bases. During the process of synthesizing these bases using photolithography, however, slight overlap of light may occur at edges of optical masks. As a result, the boundary between the first and second feature may contain probes having sequences of bases that are neither the first or second sequences, or some probes intended to have the first sequence may have the second sequence, or vice versa. In a case in which a checkerboard pattern of probes was intended to be synthesized, it may be assumed for illustrative purposes that the second feature was intended not to have probes so that the feature would appear dim after hybridization and scanning. If photolithographic overlap occurred, however, some probes having all or a part of the sequence of bases of the adjoining probes in the first feature may have been synthesized within the second feature at its boundary with the first feature. Thus, upon hybridization and scanning, the boundary between the first and second features might appear indistinct rather than crisp. That is, the bright first feature may appear to overlap into the second feature.

The fuzziness of edges, whether due to photolithographic overlap or to other sources of noise at feature boundaries, may be exacerbated if the dynamic range of the scanner is exceeded. As one example of how this situation may occur, it is assumed that probes within the second feature near its boundary with the first (hereafter, referred to as unintended edge probes) are synthesized such that they have a sequence of bases that includes part, but generally not all, of the sequence of bases of the adjoining probes of the first feature. Thus, the unintended edge probes may not hybridize as completely with the labeled target as those of the first feature and it would therefore be expected that the edge probes would appear dimmer than the probes of the first feature. In some cases, however, the scanner may not discriminate between the bright first-feature probes and the somewhat dimmer unintended edge probes. This result may occur because the dynamic range of the scanning instrument was exceeded due to the scanner"s excitation source having been set at too high a gain, higher-than-anticipated responsiveness of the labels to the excitation source, high gain of the circuitry that detects emissions from the excited label, or for other reasons. When the dynamic range is exceeded, pixels above a saturation threshold may all appear to be equally bright even though they represent emissions of varying intensities. In such a case, bright elements may overlap onto adjoining dim elements.

These overlap effects, whatever their cause, may interfere with the implementation of conventional techniques that, for example, search for the boundaries between bright and dim elements in an alignment pattern. The unintended result may be that an alignment grid is inaccurately positioned over an image because the grid was itself inaccurately aligned with the alignment pattern.

Specific embodiments are now described that address these and other problems. An illustrative implementation of these embodiments is referred to as image alignment tool 100, aspects of which are illustrated in FIGS. 1 through 7B. Alignment tool 100 adjusts the alignment of a grid with an image. The grid includes a plurality of grid elements and the image includes a plurality of image features comprised of pixels. As shown in FIG. 2, tool 100 of the illustrated embodiment includes an initial grid aligner 210 that determines an initial position of the grid such that the grid elements are at least approximately aligned with the image features. Tool 100 also includes a grid offsetter 220 that determines one or more additional positions of the grid that each are offset from the initial position and from each other. Another element of tool 100 is intensity scorer 230 that determines a set of intensity scores for test grid elements selected from the grid elements. Each member of this set is based, at least in part, on intensities of pixels of one or more image features within the test grid element in one of the initial or additional positions. Tool 100 further includes intensity-score ranker 240 that, for each of the test grid elements, ranks the set of intensity scores with respect to each other to generate a set of rank scores for the test grid element. Another element of tool 100 is combined-rank-score generator 250 that combines, for each of the initial and additional grid positions, the members of the sets of rank scores corresponding to the grid position, thus generating a combined rank score for the grid position. Yet another element of tool 100 is grid alignment adjuster 260 that adjusts the alignment of the grid based, at least in part, on a comparison among the combined rank scores of the initial and additional grid positions. Illustrative embodiments of each of these elements of tool 100 are described in greater detail below.

Image alignment tool 100 may be implemented in hardware, software, firmware, or any combination thereof. In the illustrated embodiment, it generally is assumed for convenience that tool 100 is implemented in software. Thus, software-implemented functional elements perform the operations of tool 100. That is, the functional elements of the illustrated embodiment comprise sets of software instructions that cause the described functions to be performed. These software instructions may be programmed in any programming language, such as C++ or another high-level programming language. Tool 100 may therefore be referred to as a set of image alignment instructions, and its functional elements may similarly be described as sets of instructions for execution by computer 103.

Figure 2:
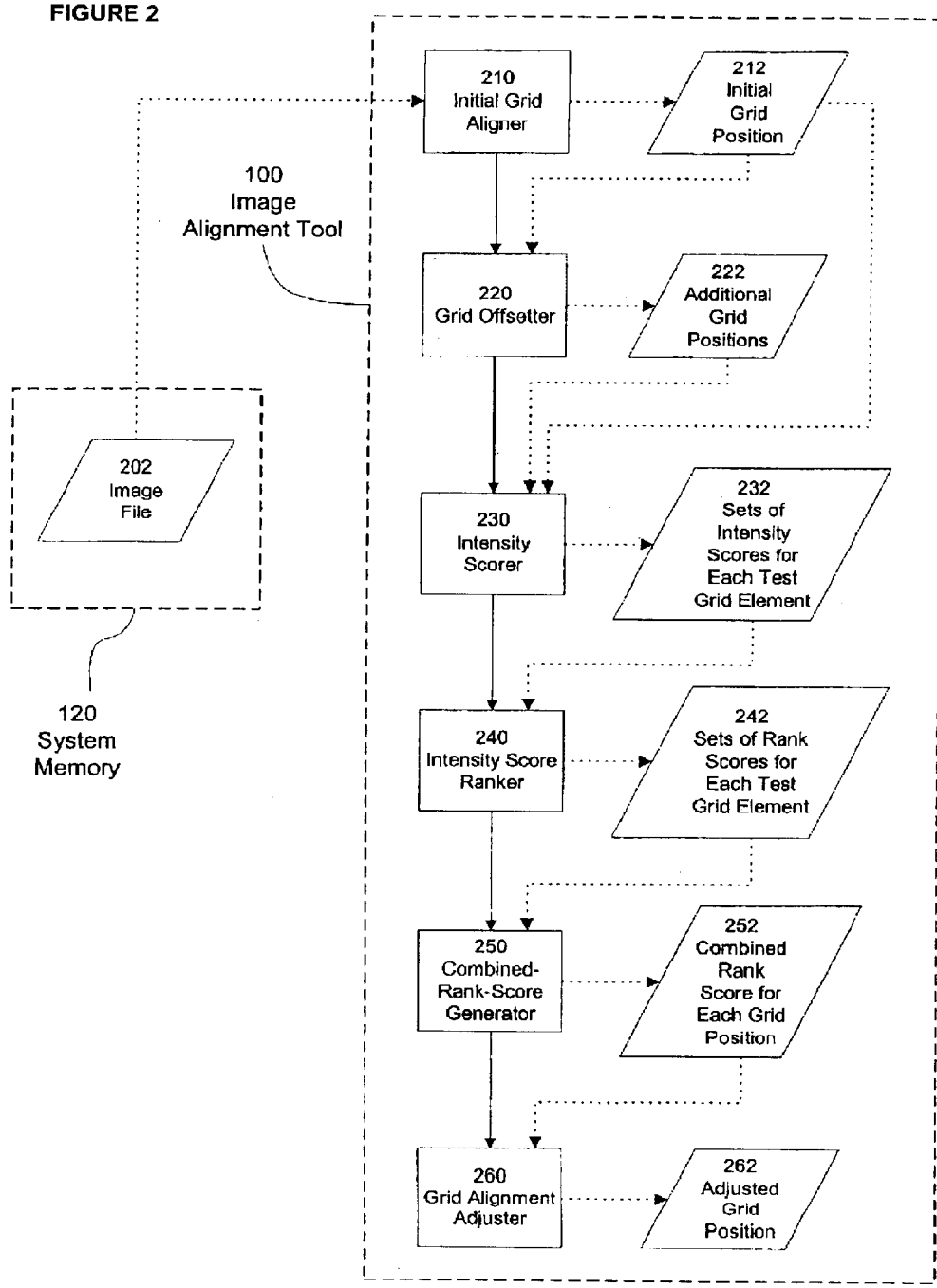
FIG. 2 is a functional block diagram of one embodiment of an image alignment tool in accordance with the present invention, such as may be implemented with the computer system of FIG. 1.

Computer103 Computer 103, shown in FIG. 1, may be a computing device specially designed and configured to support and execute some or all of the functions of image alignment tool 100. Computer 103 also may be any of a variety of types of general-purpose computers such as a personal computer, network server, workstation, or other computer platform now or later developed. Computer 103 typically includes known components such as a processor 105, an operating system 110, a graphical user interface (GUI) controller 115, a system memory 120, memory storage devices 125, and input-output controllers 130. It will be understood by those skilled in the relevant art that there are many possible configurations of the components of computer 103 and that some components that may typically be included in computer 103 are not shown, such as cache memory, a data backup unit, and many other devices.

Processor 105 may be a commercially available processor such as a Pentium® processor made by Intel Corporation, a SPARC® processor made by Sun Microsystems, or it may be one of other processors that are or will become available. Processor 105 executes operating system 110, which may be, for example, a Windows®-type operating system from the Microsoft Corporation; a Unix® or Linux-type operating system available from many vendors; another or a future operating system; or some combination thereof. Operating system 110 interfaces with firmware and hardware in a well-known manner, and facilitates processor 105 in coordinating and executing the functions of various computer programs that may be written in a variety of programming languages. Operating system 110, typically in cooperation with processor 105, coordinates and executes functions of the other components of computer 103. Operating system 110 also provides scheduling, input-output control, file and data management, memory management, and communication control and related services, all in accordance with known techniques.

System memory 120 may be any of a variety of known or future memory storage devices. Examples include any commonly available random access memory (RAM), magnetic medium such as a resident hard disk or tape, an optical medium such as a read and write compact disc, or other memory storage device. Memory storage device 125 may be any of a variety of known or future devices, including a compact disk drive, a tape drive, a removable hard disk drive, or a diskette drive. Such types of memory storage device 125 typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device 125.

In some embodiments, the present invention includes a computer program product comprising a computer usable medium having control logic (computer software program, including program code) stored therein. The control logic, when executed by processor 105, causes processor 105 to perform some of the functions of the invention, as described herein. In other embodiments, some functions of the present invention are implemented primarily in hardware using, for example, a hardware state machine. Implementation of the hardware state machine so as to perform the functions described herein will be apparent to those skilled in the relevant arts.

Input-output controllers 130 could include any of a variety of known devices for accepting and processing information from a user, whether a human or a machine, whether local or remote. Such devices include, for example, modem cards, network interface cards, sound cards, or other types of controllers for any of a variety of known input devices 102 such as a keyboard, mouse, touch-screen display, touch pad, or microphone with a voice recognition device. Output controllers of input-output controllers 130 could include controllers for any of a variety of known display devices 180 for presenting information to a user, whether a human or a machine, whether local or remote. Display devices 180 could include, for example, a video monitor, printer, audio speaker with a voice synthesis device, network connection, or modem connection. If one of display devices 180 provides visual information, this information typically may be logically and/or physically organized as an array of picture elements, sometimes referred to as pixels. Graphical user interface (GUI) controller 115 may comprise any of a variety of known or future software programs for providing graphical input and output interfaces between computer 103 and a user, and for processing user inputs.

In the illustrated embodiment, the functional elements of computer 103 communicate with each other via system bus 104. Some of these communications may be accomplished in alternative embodiments using network or other types of remote communications. Also, various other known communication buses, channels, and connections may also be used in a known manner instead of, or in conjunction with, system bus 104.

It will be understood by those skilled in the relevant art that the functions ascribed to image alignment tool 100, if implemented in software, typically are performed by processor 105 of computer 103 executing the set of image alignment instructions, typically in cooperation with operating system 110 of computer 103. Henceforth, the fact of this cooperation between processor 105 and operating system 110 may not be repeated or further described, but will be understood to be implied. It will also be evident to those skilled in the relevant art that, if implemented in software, image alignment tool 100 may be loaded into system memory 120 and/or memory storage device 125 through one of input devices 102. All or portions of tool 100 may also reside in a read-only memory or similar device of memory storage device 125, such devices not requiring that tool 100 first be loaded through input devices 102. It will be understood by those skilled in the relevant art that tool 100, or portions of it, may be loaded by processor 105 in a known manner into system memory 120, or cache memory (not shown), or both, as advantageous for execution.

Initial Grid Aligner 210 As noted, initial grid aligner 210, shown in FIG. 2, determines an initial position of the grid such that the grid elements are at least approximately aligned with image features. The techniques described in U.S. Pat. No. 6,090,555 may be used for this initial alignment, as well as any of a number of other known alignment techniques or ones that may be developed in the future. The initial alignment typically is computer-implemented, but may also be accomplished in whole or in part by human intervention. For example, a person may accomplish some or all of the functions of initial grid aligner 210 by providing an initial alignment. This alignment may be done by pointing a cursor or otherwise interacting with computer 103 in accordance with any of a variety of conventional user-interface techniques. One or more of GUI's 182 may be employed for these purposes in accordance with conventional techniques.

In addition, one or more functions of the present invention may themselves be used for the initial alignment. For example, grid aligner 210 may arbitrarily position a grid and proceed to attempt to identify and validate a known pattern as exemplified in step 705 of FIG. 7A, and as described in greater detail below with respect to the particular implementation of step 705 shown in FIG. 7B. If, in this example, it is determined in step 760 of FIG. 7B that the known pattern has not been validated, then initial grid aligner 210 may employ any of a variety of known search techniques to adjust the initial position of the grid. For example, the initial alignment may systematically be moved in either or both of the X and Y positions and the validation process repeated. This procedure may be repeated for as many iterations as is necessary until validation is achieved, or the procedure may be stopped after a determined number of iterations. This latter option may be desirable to account for the possibility that the known pattern is not present. This situation may be encountered due to a variety of causes, such as malfunction of the scanning system, failure of the synthesis of the known pattern, or failure of the hybridization process intended to generate the known pattern.

Figure 3A:
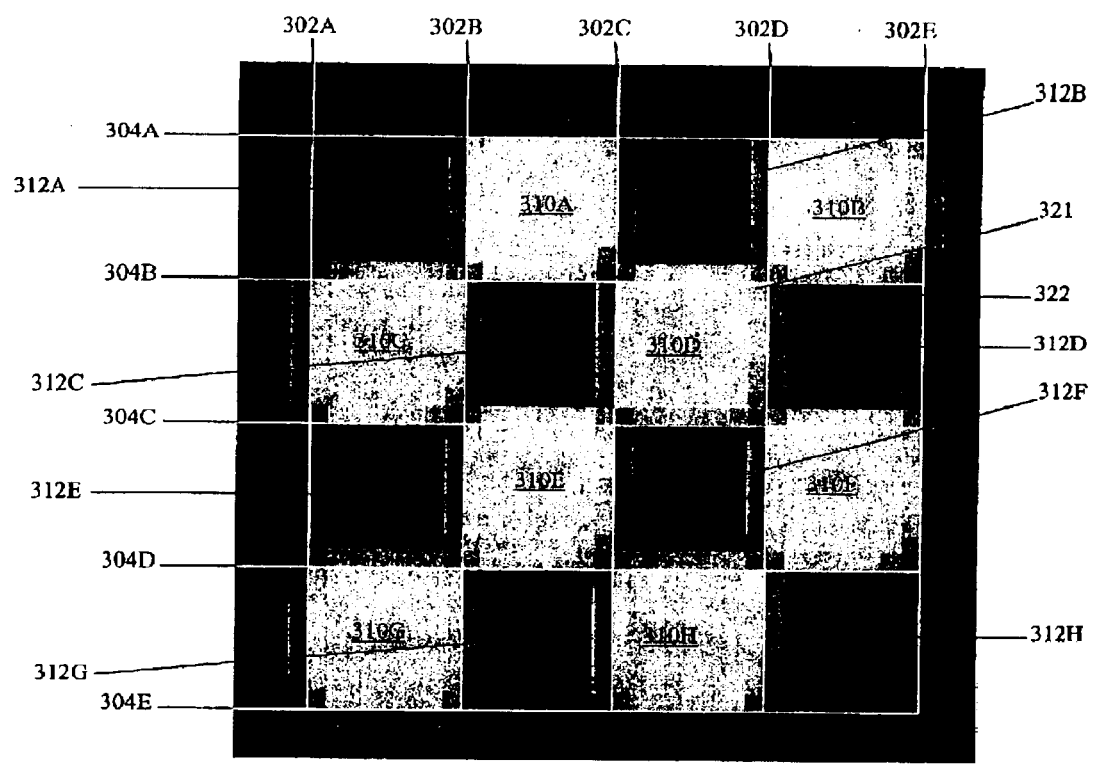
FIG. 3A is a graphical representation of one embodiment of an image that has been constructed from an image file and initially aligned with a grid in accordance with the image alignment tool of FIG. 2.

FIG. 3A is a graphical representation of an illustrative image that has been initially aligned with a grid by initial grid aligner 210. The image of FIG. 3A may be displayed or otherwise presented on one of output devices 180, such as a video monitor. Initial grid aligner 210 in this illustrative implementation constructs the image from image file 202 in accordance with known techniques. It is assumed for illustrative purposes that scanning system 160 has caused image file 202 to be stored in system memory 120 of computer 103. Scanning system 160 may comprise any of a variety of known scanning devices, such as any of those described or mentioned in U.S. Pat. Nos. 5,143,854; 5,578,832; 5,631,734; 5,834,758; 5,981,956 and 6,025,601, and in PCT Application PCT/US99/06097, incorporated by reference above. Scanning system 160 may also comprise a scanning device to be developed in the future.

Initial grid aligner 210 superimposes grid axes over the image using conventional techniques. In this example, horizontal and vertical grid axes define elements of the grid. Vertical axes 302A, 302B, 302C, 302D, and 302E are hereafter generally and collectively referred to as vertical axes 302. Similarly, horizontal axes 304A–304E are generally and collectively referred to as horizontal axes 304. Vertical axes 302 and horizontal axes 304 define grid elements 310A–310H and 312A–312H, generally and collectively referred to as grid elements 310 and 312, respectively. Although grid elements 310 and 312 are square in this example, they may be other shapes in alternative implementations.

The image shown in FIG. 3A is made up of pixels, such as pixels 321 and 322. In this example, each pixel is square, although it need not be so in other implementations. As noted above with respect to the illustrative implementation, a pixel at a particular location on the image has a single luminance value representative of a characteristic of emissions, such as intensity, detected at a corresponding location on the scanned substrate.

FIG. 4A is a simplified graphical representation of an idealized version of the image of FIG. 3A showing, by numerical representations, intensity values of pixels in the file. In the idealized image of FIG. 4A, all of the pixels of grid elements 310C and 310D are uniformly bright (as arbitrarily represented by the value 4), and all of the pixels of grid element 312C are uniformly dim (as arbitrarily represented by the value 0). The features in this idealized image thus are uniform and conform precisely to a square pattern, and this pattern conforms precisely to the grid alignment. That is, each grid element is superimposed precisely over an image feature. In particular, grid elements 310C and 310D are precisely positioned over bright image features and grid element 312C is precisely positioned over a dim image feature.

The idealized image features of FIG. 4A may illustratively be assumed to represent emissions detected from corresponding probe features synthesized on a substrate in square patterns. For example, many thousands, or millions, of nucleotide probes having a first sequence may be assumed to have been synthesized or otherwise placed on square areas of a substrate corresponding to the areas of image features contained within grid elements 310C and 310D. Probes having a second nucleotide sequence may be assumed to have been synthesized on a square area of the substrate corresponding to the area of the image feature contained within grid element 312C. In this example, it is further assumed that a target has strongly hybridized to the two square probe features having the first nucleotide sequence, and that the target has not hybridized to the square probe feature having the second nucleotide sequence. Thus, the scanning system has detected high intensity emissions from the two probe features corresponding to the image features within grid elements 310C and 310D and low intensity (or no) emissions from the probe feature corresponding to the image feature within grid element 312C.

The image features of FIG. 3A do not correspond to the idealized image features of FIG. 4A; i.e., patterns of bright and dim pixels in FIG. 3A do not fix precisely into square patterns of consistent dimensions. This imprecision of the features of FIG. 3A may be due to any of a number of causes. One cause may be that the probe features represented by the image of FIG. 3A were not perfectly synthesized in square patterns of a same nucleotide sequence. For example, in a particular synthesis method, light reflections or other effects may occur at mask boundaries during the photolithographic synthesis of probe features. Effected probes at the mask boundaries may therefore not have the intended nucleotide sequence and thus may not hybridize to the target in the intended manner. Another reason for the disparity between the idealization of FIG. 4A and the image of FIG. 3A may be that the scanning system experienced mechanical jitter due to any of a variety of reasons, such as uncompensated non-linearities in galvanometer performance, uncompensated external influences, calibration errors, and so on. Thus, the scanning system may identify emissions from a particular location as having originated from a neighboring location where emissions in fact did not occur. One result may be blurring of the image feature and its apparent enlargement.

Yet another reason for the disparity between FIGS. 4A and 3A may be that the scanning system has exceeded its dynamic range when detecting emissions. For example, the range of intensities between very dim features and very bright features may exceed the linear operating range of the scanning system so that saturation occurs with respect to bright pixels. In this case, a pixel representing emissions of medium intensity may be represented as having brightness nearly the same as that of a pixel representing emissions of very high intensity. One possible result is that image features corresponding to probe features that hybridized relatively strongly with the target will appear to be significantly larger than image features corresponding to probe features that hybridized relatively weakly with the target. These effects may occur in the scanning of probe arrays made in accordance with a wide range of techniques, such as, to provide non-limiting examples, synthesis techniques or spotting methods involving ink-jet techniques. As noted above, the present invention is generally applicable irrespective of the techniques used to make or scan the probe arrays, and the illustrated implementations are illustrative only.

For illustrative purposes, FIG. 4B provides a representation of image pixel values that, while simplified, more closely corresponds to the non-ideal image of FIG. 3A than does FIG. 4A. For example, some pixels within grid element 310C of FIG. 4B are shown as having intensity values less than 4, roughly corresponding to the varying intensities of the pixels within grid element 310C of FIG. 3A. However, the alignment of the grid is illustratively assumed to be the same in FIG. 4B as in FIG. 3A. For example, pixel 321 occupies the upper right corner of grid element 310D in both figures. Thus, FIG. 4B, like FIG. 3A, represents an illustrative initial alignment in which the grid is at least approximately aligned with the image features.

Figure 6:
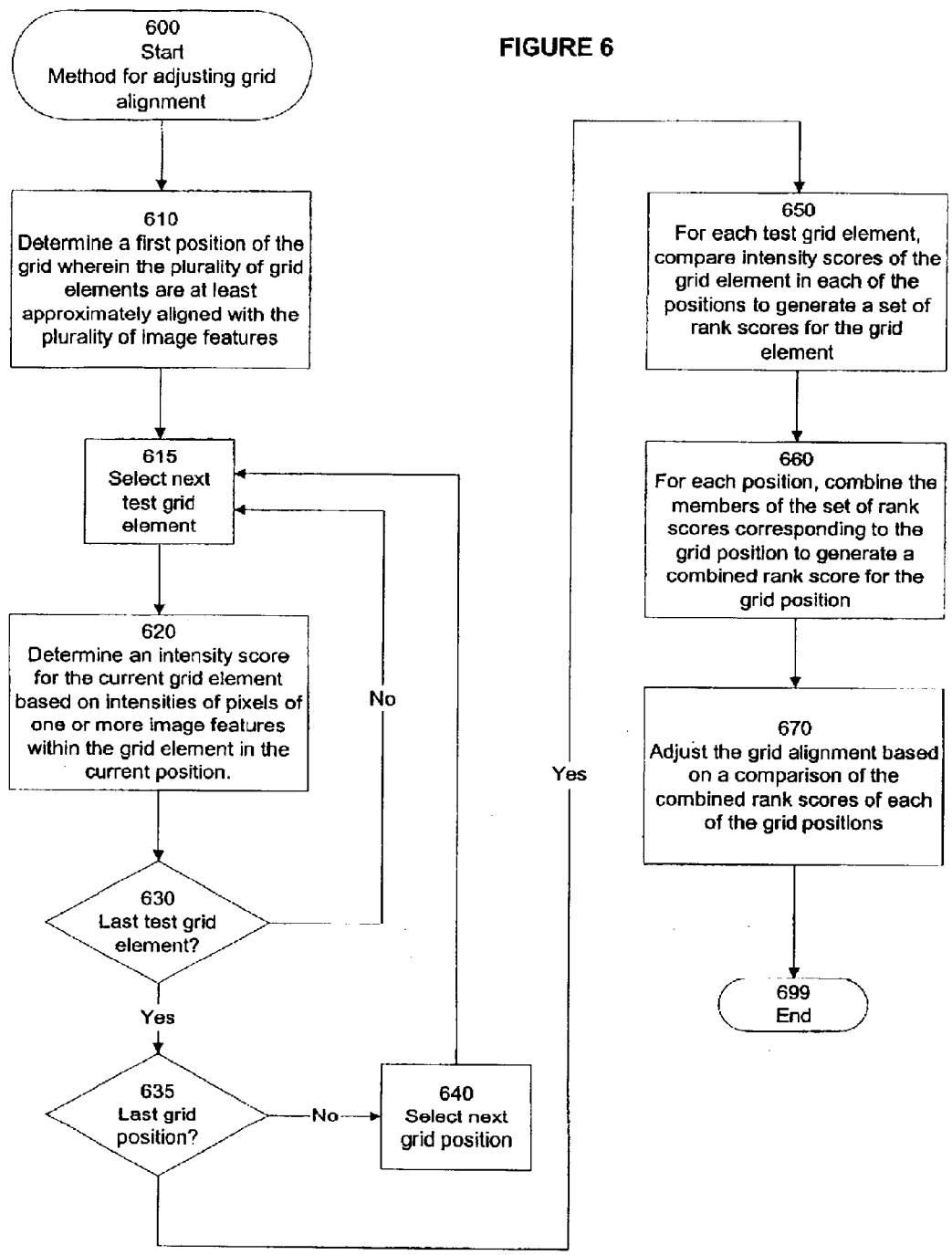
FIG. 6 is a flow diagram of one embodiment of a method for adjusting grid alignment such as may be implemented by the image alignment tool of FIG. 2.
Figure 7A:
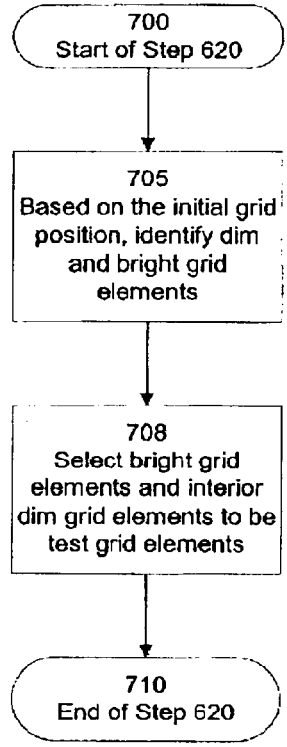
FIG. 7A is a flow diagram of one embodiment of an intensity-score-determination step, such as shown in FIG. 6.
Figure 7B:
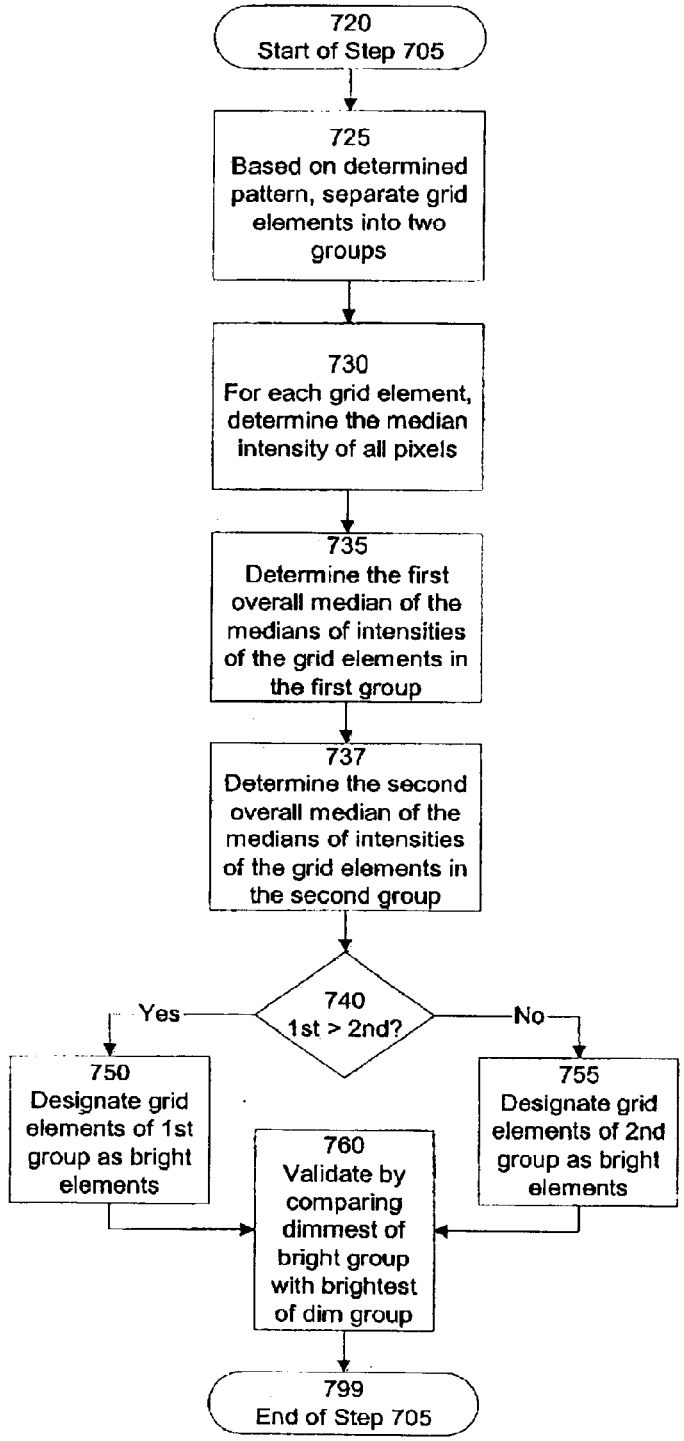
FIG. 7B is a flow diagram of one embodiment of a grid-element identification step, such as shown in FIG. 7A.

Method step 610, shown in FIG. 6, represents the step of initially aligning the grid in accordance with the functions just described with respect to the operations of initial grid aligner 210. For convenience, reference may hereafter be made only parenthetically to other method steps or decision elements corresponding to other described functions of elements of tool 100. It will be understood that many methods are possible for implementing the functions of tool 100, and that the method steps and decision elements of FIGS. 6, 7A, and 7B are illustratively only. Similarly, many arrangements of functional elements are possible for implementing the method of FIGS. 6, 7A, and 7B and of other methods encompassed within the present invention. The arrangements of elements shown in FIGS. 1 and 2 are illustrative only.

Grid Offsetter 220 Grid offsetter 220, as noted above, determines one or more additional positions of the grid that each are offset from the initial position and from each other. (See corresponding method step 640.) In the illustrated implementation, this offsetting is done by systematically moving the grid in the X (e.g., horizontal) and/or Y (e.g., vertical) directions. Each move is made, in this implementation, in units of one or more pixels in one or both directions. Movement in fractions of pixels is possible in other implementations. In the illustrated implementation, the total range of horizontal movement typically need not exceed half the width of a graphical element in either the left or right direction. Vertical movement similarly typically need not exceed half the height of a graphical element in either the up or down direction. Greater ranges of movements generally are not desirable, as the approximate initial alignment of graphical elements with image features thus may be lost. Indeed, in practice it is observed the range of movement in any direction need not be greater in some applications than a value approximately equal to one-third the height or width of a graphical element.

Figure 3B:
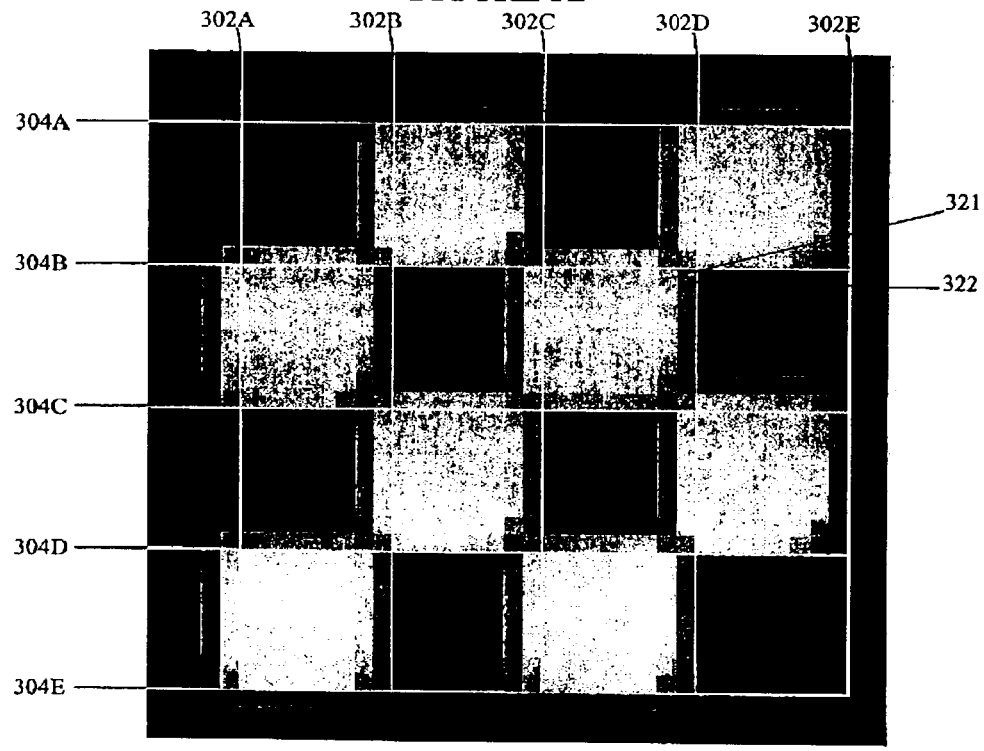
FIG. 3B is a graphical representation of the image of FIG. 3A, except that the grid has been offset by one pixel.

FIG. 3B is a graphical representation of the same image as shown in FIG. 3A, except that grid offsetter 220 has moved the grid one pixel to the right. Thus, whereas pixel 321 is located in the upper right corner of grid element 310D in FIG. 3A, pixel 322 is located in the upper right corner of that grid element in FIG. 3B.

FIG. 4C is an idealized version of FIG. 3B. Thus, FIG. 4C represents the same idealized image as shown in FIG. 4B except that grid offsetter 220 has moved the grid one pixel to the right. The idealized representations of the pixels in FIGS. 4B and 4C are the same. The reference numbers of grid elements of FIG. 4C are primed, however, to distinguish them from the corresponding grid elements of FIG. 4B since the pixels encompassed within the grid elements are not the same in the two figures. For example, grid element 310C' of FIG. 4C corresponds to grid element 310C of FIG. 4B, but the former is shifted one pixel to the right in relation to the latter and thus does not encompass the same pixels.

In any systematic manner, i.e., any manner in which all desired additional grid positions are achieved (see step 615 and decision element 630), grid offsetter 220 moves the grid by additional pixel increments. In the illustrated implementation, a grid element has a width equal to eight pixels and a height equal to eight pixels. Consistent with the observation noted above regarding movement in any direction of no more than about one-third the height or width, grid offsetter 220 of the illustrated implementation moves the grid so that it occupies each position three pixels to the right or left, and three pixels above or below, the initial position. Thus, there are 36 additional positions in this example.

Information about the characteristics of pixels within each of the grid elements, in each of successive grid positions, may be stored for later processing in accordance with known techniques. Alternatively, some calculations performed by other elements of tool 100 may be carried out for each grid position prior to grid offsetter 220 moving the grid to another position and thus initiating another set of similar calculations. As will be appreciated by those of ordinary skill in the relevant art, there are numerous combinations of techniques that may be employed for storing and calculating data at the initial and additional grid positions. Thus, the approach represented by the flow diagram of FIG. 6 will be understood to be exemplary only.

Intensity Scorer 230 Intensity scorer 230 determines a set of intensity scores for test grid elements selected from the grid elements (see step 620). Each member of this set is based, at least in part, on intensities of pixels of one or more image features within the test grid element in one of the initial or additional positions.

In some implementations, test grid elements need not be selected; e.g., intensity scorer 230 may determine sets of intensity scores for each of the grid elements. However, selection of test grid elements may be desirable due to boundary or other effects. For example, in the illustrated implementation in which probe features have been synthesized in a checkerboard pattern, dim features on the periphery of the checkerboard are typically surrounded by dim areas in which probe features were not synthesized. Thus, the dim features on the periphery are ill defined in the sense that they are not easily distinguished from dim areas outside the checkerboard pattern. In other words, adjusting the alignment of dim features on the periphery is problematic because dim areas containing no signal, or containing only noise, may be interpreted as a signal, i.e., a part of the checkerboard. In contrast, dim features in the interior of the checkerboard pattern are surrounded on all sides by bright features, and bright features both on the periphery and in the interior are surrounded on all sides by dim features.

To select the test grid elements, intensity scorer 230 first determines which of the features of the checkerboard pattern are dim and which are bright based on the initial grid position (see step 705). This process is illustratively accomplished by separating the grid elements, which are presumed to be disposed approximately in alignment with the checkerboard features, into two groups based on the known checkerboard geometry (see step 725). Thus, in the example of FIG. 3A, grid elements 312 are assigned to one group and grid elements 310 are assigned to the other group. At this point, it is not presumed that grid elements 312 are dim and grid elements 310 are bright. Rather, a checkerboard pattern of intensities opposite to those shown in FIG. 3A (i.e., in which grid elements 312 are bright and grid elements 310 are dim) may be employed for various reasons relating, for example, to the type of labels or probes used. Also, as noted, many patterns other than checkerboards may be used in other implementations, and many other techniques may thus be used in those implementations for initially separating the grid elements into groups based on presumed commonality of values.

In order to identify grid elements 310 and 312 as dim or bright, intensity scorer 230 of the illustrative implementation determines a median intensity for each grid element in both groups (see step 730). An element's median intensity is determined, in this implementation, based on the intensity of each pixel in the element. The median is used in the illustrative implementation to reduce the affects of aberrant pixel values that may occur, particularly around the periphery of the element. In other implementations, not all of the pixels of a grid element need be considered, and/or statistical measures other than the median may be used to characterize the intensity of an element.

Intensity scorer 230 then determines the overall median of the medians (see steps 735 and 737) for each of the two groups. These two overall medians are then compared with each other (see decision element 740). The group having the overall median of greater magnitude is designated as the group of bright grid elements, and the other group is designated as the group of dim grid elements (see steps 750 and 755). In this implementation, intensity scorer 230 validates these designations by comparing the dimmest grid element of the bright group (i.e., the element having the lowest median) with the brightest grid element of the dim group. An error condition may be declared, in accordance with techniques known to those of ordinary skill in the relevant art, if the dimmest grid element of the bright group is equal to or dimmer than the brightest grid element of the dim group (see step 760). Having identified the dim and bright groups, and based on the known checkerboard pattern of this illustrative example, intensity scorer 230 thus selects the bright grid elements (elements 310 in the example of FIG. 3A) and the interior dim grid elements (elements 312C and 312F of FIG. 3A) to be the test grid elements (see step 708).

Intensity scorer 230 stores data, in accordance with known techniques, representing the intensities of pixels contained within each test grid element in the initial grid position. In the illustrated implementation, this data consists of a mean intensity value, referred to hereafter as an intensity score, for each grid element based on all of the pixels within the grid element. By using the mean as the measure of intensity, the intensity values of pixels around the periphery of the grid element may have greater influence than if the median of pixel intensity values had been used. Because the values of pixels at the periphery may be of particular importance in determining best alignment with a feature, the mean may thus be preferable to the median in this aspect of the operations of intensity scorer 230. However, in other implementations, a measure other than the median may be employed, and fewer than all pixels may be considered. In a similar manner, intensity scorer 230 determines and stores an intensity score for the pixels contained within each test grid element in each additional grid position determined by grid offsetter 220. A set of intensity scores is thus stored for each test grid element, with each member of the set for a particular element representing the intensity score of that element in a particular grid position. These data are represented in FIG. 2 as sets of intensity scores 232. It will be understood that any of a variety of known techniques, or techniques to be developed in the future, may be used for organizing and/or storing these data.

FIGS. 5A and 5B are tables that shows illustrative intensity scores for illustrative test grid elements 310C, 312C, and 310D in two illustrative grid positions. The grid positions upon which FIGS. 5A and 5B are based are the ones shown respectively in FIGS. 4B and 4C, which, as noted, correspond respectively with FIGS. 3A and 3B. The pixel intensities used by intensity scorer 230 to determine these intensity scores are shown in FIG. 5A for the grid position of FIG. 4B and in FIG. 5B for the grid position of FIG. 4C. Thus, as one example, the set of intensity scores for test grid element 310C includes the two set members 3.6875 (the mean pixel intensity in the grid position of FIG. 4B) and 3.5938 (the mean pixel intensity in the grid position of FIG. 4C). It will be understood that additional set members, not shown, may be determined by intensity scorer 230 for test grid element 310C in additional grid positions.

Intensity-Score Ranker 240For each of the test grid elements, intensity-score ranker 240 ranks the set of intensity scores with respect to each other to generate a set of rank scores for the test grid element (see corresponding step 650 of FIG. 6). In the illustrated implementation, intensity-score ranker 240 assigns a value of 1 to the brightest member of a set of intensity scores for a test grid element identified by intensity scorer 230 as being a bright element. The next brightest member of this set is ranked 2, and so on. Thus, because test grid element 310C is identified as bright in this example, the intensity score 3.6875 is ranked 1 and the intensity score 3.5938 is ranked 2. In the illustrated implementation, intensity-score ranker 240 assigns a value of 1 to the dimmest member of a set of intensity scores for a test grid element identified by intensity scorer 230 as being a dim element. The next dimmest member of this set is ranked 2, and so on. Thus, because test grid element 312C is identified as dim in this example, the intensity score 1.5781 is ranked 1 and the intensity score 1.7656 is ranked 2. As will be evident to those of ordinary skill in the art, this scheme is but one of many that could be employed to provide rankings that contrast the intensities of pixels contained within grid elements identified as bright and dim. The scheme described with respect to the present implementation is generally advantageous because the ranking indicates the grid position for each grid element that provides the greatest degree of contrast. That is, the ranking indicates, for each grid element, the position of brightest bright or dimmest dim. Combined-Rank-Score Generator 250 Combined-rank-score generator 250 combines, for each of the initial and additional grid positions, the members of the sets of rank scores corresponding to the grid position, thus generating a combined rank score for the grid position (see step 660). In the illustrated implementation, this combining is accomplished by addition, but other approaches, such as weighted addition (i.e., some set elements, for example the interior dim elements, given prominence as compared to others), could be employed in alternative implementations. The common objective of the present implementation and alternative approaches is to identify the grid position that provides an overall combination of brightest bright and dimmest dim grid elements as compared to any other grid position.

With respect to the illustrated implementation indicated in the table of FIG. 5A, generator 250 generates a combined rank score of 3 for the grid position shown in FIG. 4B by simple addition of the rank scores of each of the test grid elements in this grid position. It will be understood that the combined rank score for the corresponding checkerboard pattern of FIG. 3A would include the rank scores for all test grid elements and not just for the three illustrative ones shown in FIG. 4A. As indicated in the table of FIG. 5B, generator 250 similarly generates an illustrative combined rank score of 6 for the grid position shown in FIG. 4C.

Grid Alignment Adjuster 260As noted, grid alignment adjuster 260 adjusts the alignment of the grid based, at least in part, on a comparison among the combined rank scores of the initial and additional grid positions (see step 670). In the present implementation, this comparison is accomplished by determining the lowest combined rank score. Grid alignment adjuster 260 adjusts the grid to the position having this lowest combined rank score. Thus, in the simplified example of FIGS. 5A and 5B, grid alignment adjuster 260 selects the grid position of FIG. 4B as the adjusted grid position because its combined rank score is lower than that of the other grid position. Generally speaking, this lowest combined rank score indicates that the corresponding grid position has some combination (determined by the schemes used by scorer 230, ranker 240, and/or generator 250) of the brightest bright grid elements and dimmest dim grid elements as compared to all other grid positions. In the case in which two or more of the grid positions have the same lowest combined rank score, any of a variety of techniques may be used to select one. These techniques may include, for example, selecting the position closest to the initial position, selecting the position based on a preferred orientation, such as closest to the upper left, or selecting it arbitrarily.

Having described various embodiments and implementations of the present invention, it should be apparent to those skilled in the relevant art that the foregoing is illustrative only and not limiting, having been presented by way of example only. Many other schemes for distributing functions among the various functional elements of the illustrated embodiment are possible in accordance with the present invention. The functions of any element may be carried out in various ways in alternative embodiments. Also, the functions of several elements may, in alternative embodiments, be carried out by fewer, or a single, element.

For example, for purposes of clarity the functions of alignment tool 100 are described as being implemented by the functional elements shown in FIG. 2. However, the invention need not be divided into these distinct functional elements. Similarly, operations of a particular functional element that are described separately for convenience need not be carried out separately. For example, some or all of the functions of intensity-score ranker 240 could be implemented by combined rank-score generator 250, and vice versa. Similarly, in some embodiments, any functional element may perform fewer, or different, operations than those described with respect to the illustrated embodiment. Also, functional elements shown as distinct for purposes of illustration may be incorporated within other functional elements in a particular implementation. For example, image alignment tool 100 and/or computer 103 may be a component of scanning system 160, although they are shown separately in FIG. 1 for purposes of illustration. As noted, image alignment tool 100 may be implemented in hardware, firmware, software, or a combination thereof, and thus may be included in computer 103 although shown separately for purposes of illustration.

Also, the sequencing of functions or portions of functions generally may be altered. For example, the method steps shown in FIGS. 6, 7A and 7B generally need not be carried out in the order suggested by the figures. Among many possible examples, decision element 635 could be invoked before decision element 630, steps 615 and 640 could be interchanged in FIG. 6, and so on.

Certain functional elements, data structures, and so on, may be described in the illustrated embodiment as located in system memory 120 or memory storage device 125 of computer 103. In other embodiments, however, they may be located on, or distributed across, computer systems or other platforms that are remote from computer 103. For example, any one or more of data files or data structures 202, 212, 222, 232, 242, 252, and/or 262 may be located in a computer system or systems remote from computer 103. In those cases, the operations of image alignment tool 100 with respect to processing and/or displaying information stored in these data files or data structures may be carried out over a network or by any of numerous other known means for transferring data and/or control to or from a remote location.

In addition, it will be understood by those skilled in the relevant art that control and data flows between and among functional elements of the invention and various data structures may vary in many ways from the control and data flows described above. More particularly, intermediary functional elements (not shown) may direct control or data flows, and the functions of various elements may be combined, divided, or otherwise rearranged to allow parallel processing or for other reasons. Also, intermediate data structures or files may be used, various described data structures or files may be combined, the sequencing of functions or portions of functions generally may be altered, and so on. Numerous other embodiments, and modifications thereof, are contemplated as falling within the scope of the present invention as defined by appended claims and equivalents thereto.

What is claimed is:

1. A method for adjusting the alignment of a grid with an image, wherein the grid includes a plurality of grid elements and the image includes a plurality of image features comprised of pixels, comprising the steps of:
   (1) determining an initial position of the grid;
   (2) determining one or more additional positions of the grid that are offset from the initial position and from each other;
   (3) determining a set of intensity scores for each of a plurality of test grid elements of the plurality of grid elements, wherein at least one member of the set is based, at least in part, on intensities of pixels of one or more image features within the test grid element in one of the initial or additional positions;
   (4) ranking the set of intensity scores with respect to each other to generate a set of rank scores for the test grid element;
   (5) combining the members of the sets of rank scores corresponding to the grid position to generate a combined rank score for the grid position for each of the initial and additional grid positions; and
   (6) adjusting the alignment of the grid based on a comparison among the combined rank scores of the initial and additional grid positions.

2. The method of claim 1, wherein:
step (2) comprises the step of moving the grid from the first grid position in a positive or negative X direction by a value substantially equal to a span of one or more pixels, or moving the grid from the first grid position in a positive or negative Y direction by a value substantially equal to a span of one or more pixels.

3. The method of claim 2, wherein:
the test grid elements each have a first length in the X direction and a second length in the Y direction; and
step (2) further comprises moving the grid from the first grid position in the positive or negative X direction by a value no greater than approximately half the first length, or moving the grid from the first grid position in the positive or negative Y direction by a value no greater than approximately half the second length.

4. The method of claim 1, wherein:
step (3) includes the step of determining, for at least one member of the set of intensity scores, a mean of intensity values of pixels within the test grid element.

5. The method of claim 1, wherein:
step (3) includes the steps of
   (a) based on the initial grid position, identifying each of the plurality of grid elements as either a dim grid element or, in the alternative, a bright grid element; and (b) selecting the test grid elements based, at least in part, on including dim grid elements when they are bordered on all sides by a bright grid element.

6. The method of claim 5, wherein:
step (3)(a) comprises the steps of
(i) associating each of the plurality of grid elements with one of either a first element group or a second element group based on a determined pattern;
(ii) determining a first intensity of one or more of the grid elements in the first element group and a second intensity of one or more of the grid elements in the second element group;
(iii) comparing the first and second intensities;
(iv) designating the grid elements in the first element group as dim grid elements when the first intensity is less than the second intensity and as bright grid elements when the first intensity is greater than the second intensity; and
(v) designating the grid elements in the second element group as dim grid elements when the second intensity is less than the first intensity and as bright grid elements when the second intensity is greater than the first intensity.

7. The method of claim 6, wherein:
step (3)(a)(ii) comprises determining a median of intensities of three or more pixels within each of the one or more grid elements in the first and second element groups.

8. The method of claim 6, wherein:
step (3)(a)(ii) comprises determining a median of intensities of three or more pixels within each grid element in the first and second element groups.

9. The method of claim 6, wherein:
step (3)(a)(ii) comprises determining a median of intensities of each pixel within each grid element in the first and second element groups.

10. The method of claim 8, wherein:
the first intensity comprises a first overall median of the medians of intensities of pixels within each grid element in the first element group; and
the second intensity comprises a second overall median of the medians of intensities of pixels within each grid element in the second element group.

11. The method of claim 10, wherein:
step 3(a) further comprises the step of
(vi) validating the designations of steps (iv) and (v) by determining that each of the medians of intensities of the pixels within each of the grid elements in the one of the first and second element groups designated as comprising bright grid elements is greater than each of the medians of intensities of the pixels within each of the grid elements in the other element group.

12. The method of claim 5, wherein:
step (4) further comprises the step of ranking the sets of intensity scores of test grid elements identified as dim grid elements in an opposite sense to the ranking of sets of intensity scores of test grid elements identified as bright grid elements.

13. The method of claim 1, wherein:
the image includes a checkerboard pattern comprised of alternating dim and bright image features.

14. The method of claim 1, wherein:
the image includes a first pattern; and
step (1) comprises the steps of
(a) convolving the image with a filter to generate a second image having a second pattern, (b) identifying the second pattern, and
(c) aligning the grid over the image according to a position of the second pattern.

15. The method of claim 14, wherein:
step (1)(a) comprises setting a convolved pixel to a difference in intensity between an odd pixel and an even pixel of the first pattern.

16. The method of claim 1, wherein:
the image is generated, at least in part, by scanning biological material.

17. The method of claim 16, wherein:
the biological material is labeled and the scanning includes detecting emissions from the labeled biological material.

18. An image alignment tool for adjusting the alignment of a grid with an image, wherein the grid includes a plurality of grid elements and the image includes a plurality of image features comprised of pixels, comprising:
an initial grid aligner constructed and arranged to determine an initial position of the grid;
a grid offsetter constructed and arranged to determine one or more additional positions of the grid that each are offset from the initial position and from each other;
for each of a plurality of test grid elements of the plurality of grid elements, an intensity scorer constructed and arranged to determine a set of intensity scores wherein each member of the set is based, at least in part, on intensities of pixels of one or more image features within the test grid element in one of the initial or additional positions;
for each of the test grid elements, an intensity-score ranker constructed and arranged to rank the set of intensity scores with respect to each other to generate a set of rank scores for the test grid element;
for each of the initial and additional grid positions, a combined-rank-score generator constructed and arranged to combine the members of the sets of rank scores corresponding to the grid position to generate a combined rank score for the grid position; and
a grid alignment adjuster constructed and arranged to adjust the alignment of the grid based, at least in part, on a comparison among the combined rank scores of the initial and additional grid positions.

19. The alignment tool of claim 18, wherein:
the grid offsetter further is constructed and arranged to move the grid from the first grid position in a positive or negative X direction by a value substantially equal to a span of one or more pixels, or move the grid from the first grid position in a positive or negative Y direction by a value substantially equal to a span of one or more pixels.

20. The alignment tool of claim 19, wherein:
the test grid elements each have a first length in the X direction and a second length in the Y direction; and
the grid offsetter further is constructed and arranged to move the grid from the first grid position in the positive or negative X direction by a value no greater than approximately half the first length, or moving the grid from the first grid position in the positive or negative Y direction by a value no greater than approximately half the second length.

21. The alignment tool of claim 18, wherein:
the intensity scorer further is constructed and arranged to determine, for at least one member of the set of intensity scores, a mean of intensity values of pixels within the test grid element.

22. The alignment tool of claim 18, wherein:
the intensity scorer further is constructed and arranged to identify, based on the initial grid position, each of the plurality of grid elements as either a dim grid element or, in the alternative, a bright grid element; and
select the test grid elements based, at least in part, on including dim grid elements when they are bordered on all sides by a bright grid element.

23. The alignment tool of claim 22, wherein:
the intensity scorer further is constructed and arranged to associate, based on a determined pattern, each of the plurality of grid elements with one of either a first element group or a second element group;
determine a first intensity of one or more of the grid elements in the first element group and a second intensity of one or more of the grid elements in the second element group;
compare the first and second intensities;
designate the grid elements in the first element group as dim grid elements when the first intensity is less than the second intensity and as bright grid elements when the first intensity is greater than the second intensity; and
designate the grid elements in the second element group as dim grid elements when the second intensity is less than the first intensity and as bright grid elements when the second intensity is greater than the first intensity.

24. The alignment tool of claim 23, wherein:
the intensity scorer further is constructed and arranged to determine a median of intensities of three or more pixels within each grid element in the first and second element groups, wherein the first intensity comprises a first overall median of the medians of intensities of pixels within each grid element in the first element group, and the second intensity comprises a second overall median of the medians of intensities of pixels within each grid element in the second element group.

25. The alignment tool of claim 22 wherein:
the intensity-score ranker further is constructed and arranged to rank the sets of intensity scores of test grid elements identified as dim grid elements in one sense and rank sets of intensity scores of test grid elements identified as bright grid elements in an opposite sense.

26. The alignment tool of claim 18, wherein:
the image includes a checkerboard pattern comprised of alternating dim and bright image features.

27. The alignment tool of claim 18, wherein:
the image is generated, at least in part, by scanning biological material.

28. The alignment tool of claim 27, wherein:
the biological material is labeled and the scanning includes detecting emissions from the labeled biological material.

29. A computer program product for adjusting the alignment of a grid with an image, wherein the grid includes a plurality of grid elements and the image includes a plurality of image features comprised of pixels, that, when executed on a computer system, performs a method comprising the steps of:
(1) determining an initial position of the grid wherein the plurality of grid elements are at least approximately aligned with the plurality of image features;
(2) determining one or more additional positions of the grid that each are offset from the initial position and from each other;
(3) for each of a plurality of test grid elements of the plurality of grid elements, determining a set of intensity scores wherein each member of the set is based, at least in part, on intensities of pixels of one or more image features within the test grid element in one of the initial or additional positions;
(4) for each of the test grid elements, ranking the set of intensity scores with respect to each other to generate a set of rank scores for the test grid element;
(5) for each of the initial and additional grid positions, combining the members of the sets of rank scores corresponding to the grid position to generate a combined rank score for the grid position; and
(6) adjusting the alignment of the grid based, at least in part, on a comparison among the combined rank scores of the initial and additional grid positions.

30. The computer program product of claim 29, wherein:
step (3) includes the steps of
(a) based on the initial grid position, identifying each of the plurality of grid elements as either a dim grid element or, in the alternative, a bright grid element; and
(b) selecting the test grid elements based, at least in part, on including dim grid elements when they are bordered on all sides by a bright grid element.

31. The computer program product of claim 30, wherein:
step (3)(a) comprises the steps of
(i) based on a determined pattern, associating each of the plurality of grid elements with one of either a first element group or a second element group;
(ii) determining a first intensity of one or more of the grid elements in the first element group and a second intensity of one or more of the grid elements in the second element group;
(iii) comparing the first and second intensities;
(iv) designating the grid elements in the first element group as dim grid elements when the first intensity is less than the second intensity and as bright grid elements when the first intensity is greater than the second intensity; and
(v) designating the grid elements in the second element group as dim grid elements when the second intensity is less than the first intensity and as bright grid elements when the second intensity is greater than the first intensity.

32. The computer program product of claim 29, wherein:
the image includes a first pattern; and
step (1) comprises the steps of
(a) convolving the image with a filter to generate a second image having a second pattern,
(b) identifying the second pattern, and
(c) aligning the grid over the image according to a position of the second pattern.

33. The computer program product of claim 29, wherein:
the image is generated, at least in part, by scanning biological material.

34. A method for adjusting the alignment of a grid with an image, wherein the grid includes a plurality of grid elements and the image includes a plurality of image features comprised of pixels, comprising the steps of:
(1) determining an initial position of the grid;
(2) validating that the plurality of grid elements are at least approximately aligned with the plurality of image features in the initial position;
(3) when the grid elements are not at least approximately aligned, adjusting the alignment and repeating step (2) for one or more iterations;

(4) when the grid elements are at least approximately aligned, determining one or more additional positions of the grid that each are offset from the approximately aligned position and from each other;

(5) for each of a plurality of test grid elements of the plurality of grid elements, determining a set of intensity scores wherein each member of the set is based, at least in part, on intensities of pixels of one or more image features within the test grid element in one of the initial or additional positions;

(6) for each of the test grid elements, ranking the set of intensity scores with respect to each other to generate a set of rank scores for the test grid element;

(7) for each of the approximately aligned position and additional grid positions, combining the members of the sets of rank scores corresponding to the grid position to generate a combined rank score for the grid position; and (8) adjusting the alignment of the grid based, at least in part, on a comparison among the combined rank scores of the approximately aligned and additional grid positions.

35. A computer system for processing images, comprising:

(1) a data storage device constructed and arranged to store data representing an image including a plurality of image features comprised of pixels; and (2) an image alignment tool for adjusting the alignment of a grid with the image, wherein the grid includes a plurality of grid elements and wherein the tool includes
  (a) an initial grid aligner constructed and arranged to determine an initial position of the grid wherein the plurality of grid elements are at least approximately aligned with the plurality of image features,
  (b) a grid offsetter constructed and arranged to determine one or more additional positions of the grid that each are offset from the initial position and from each other,
  (c) for each of a plurality of test grid elements of the plurality of grid elements, an intensity scorer constructed and arranged to determine a set of intensity scores wherein each member of the set is based, at least in part, on intensities of pixels of one or more image features within the test grid element in one of the initial or additional positions,
  (d) for each of the test grid elements, an intensity-score ranker constructed and arranged to rank the set of intensity scores with respect to each other to generate a set of rank scores for the test grid element,
  (e) for each of the initial and additional grid positions, a combined-rank-score generator constructed and arranged to combine the members of the sets of rank scores corresponding to the grid position to generate a combined rank score for the grid position, and
  (f) a grid alignment adjuster constructed and arranged to adjust the alignment of the grid based, at least in part, on a comparison among the combined rank scores of the initial and additional grid positions.

36. A scanning system for detecting labeled targets in probe features of a probe array, comprising:

(1) an excitation source constructed and arranged to produce emissions from one or more labeled targets;

(2) a detector constructed and arranged to detect the emissions and generate data representing one or more characteristics of the emissions;

(3) a data storage device constructed and arranged to store an image including a plurality of image features comprised of pixels based on data generated by the detector; and (4) an image alignment tool for adjusting the alignment of a grid with the image, wherein the grid includes a plurality of grid elements and wherein the tool includes
  (a) an initial grid aligner constructed and arranged to determine an initial position of the grid wherein the plurality of grid elements are at least approximately aligned with the plurality of image features,
  (b) a grid offsetter constructed and arranged to determine one or more additional positions of the grid that each are offset from the initial position and from each other,
  (c) for each of a plurality of test grid elements of the plurality of grid elements, an intensity scorer constructed and arranged to determine a set of intensity scores wherein each member of the set is based, at least in part, on intensities of pixels of one or more image features within the test grid element in one of the initial or additional positions,
  (d) for each of the test grid elements, an intensity-score ranker constructed and arranged to rank the set of intensity scores with respect to each other to generate a set of rank scores for the test grid element,
  (e) for each of the initial and additional grid positions, a combined-rank-score generator constructed and arranged to combine the members of the sets of rank scores corresponding to the grid position to generate a combined rank score for the grid position, and
  (f) a grid alignment adjuster constructed and arranged to adjust the alignment of the grid based, at least in part, on a comparison among the combined rank scores of the initial and additional grid positions.

* * * * *